United States Patent [19]
Xiong et al.

[11] Patent Number: 5,783,756
[45] Date of Patent: Jul. 21, 1998

[54] PORTABLE SAMPLER FOR VOLATILE AEROSOLS

[75] Inventors: Judy Q. Xiong, Nanuet; Beverly S. Cohen, Newburgh; Ching-Ping Fang, Nanuet, all of N.Y.

[73] Assignee: New York University, New York, N.Y.

[21] Appl. No.: 569,504

[22] Filed: Dec. 8, 1995

[51] Int. Cl.$^6$ ........................................................ G01N 1/24
[52] U.S. Cl. ................................... 73/863.23; 73/863.33
[58] Field of Search ........................... 73/862.23, 863.21, 73/863.31, 864.34, 863.33, 863.24, 863.25, 863.22

[56] References Cited

U.S. PATENT DOCUMENTS

| | | | |
|---|---|---|---|
| 4,197,098 | 4/1980 | Stiehl et al. | 73/863.24 X |
| 4,375,667 | 3/1983 | Buchan | 73/863.23 X |
| 4,432,248 | 2/1984 | Lalin | 73/863.23 X |
| 4,569,235 | 2/1986 | Conkle et al. | 73/863.23 X |
| 4,666,856 | 5/1987 | Irgum et al. | 436/122 |
| 4,786,472 | 11/1988 | McConnell et al. | 73/863.23 X |
| 4,796,475 | 1/1989 | Morpel | 73/863.22 |
| 4,980,294 | 12/1990 | Elias et al. | 436/21 |
| 5,047,073 | 9/1991 | Stetter et al. | 95/8 |
| 5,476,110 | 12/1995 | Baig et al. | 131/173 |

*Primary Examiner*—Thomas P. Noland
*Attorney, Agent, or Firm*—Eliot S. Gerber

[57] ABSTRACT

A portable air sampler to measure the concentration of a chemical compound in the air, especially in a workplace, measures the quantity of the chemical in its gas phase and in its particle phase. The sampler is connected to a pump which draws ambient air through an inlet tube and out a nozzle. A housing holds a filter aligned with the nozzle. The air is immediately separated into two parts, one portion continues straight through the filter, the second turns 180°. The particles, due to their mass and resulting inertia, will travel in the forward direction to be collected in the filter. The portion of air that flows through the filter continues through a sorbent tube where the vapor (gas phase) from this portion is collected. This sorbent tube also collects the quantity of the chemical that evaporates from the particles collected on the filter. The remainder of the air and its gas (vapor) moves upwardly and sideways to exit through an orifice and into a second sorbent tube which collects the vapor from that portion. The original phase distribution of the chemical in the air can be determined from the amounts collected on the two sorbent tubes and the known amount of air that flows through each pathway.

3 Claims, 2 Drawing Sheets

PORTABLE SAMPLER FOR VOLATILE AEROSOLS

FIELD OF THE INVENTION

The present invention relates to air sampling instruments and more particularly to portable instruments for measuring pollutants that exist in both particle and vapor phases in an atmosphere.

BACKGROUND OF THE INVENTION

At the present time there is a need for a small portable instrument which can accurately measure the phase distributed amount of certain polluting chemicals that may exist as both particle (solid or liquid phase) and vapor (gas phase) in the air.

The importance of clean air in the workplace has been recognized by the public, industrial hygiene experts and governmental bodies. The use of various chemicals in many industrial factories, fields, mines and repair shops may result in unsafe air pollution in the various workplaces. For example, polystyrene compositions are applied with spray guns in the manufacture of boats, and such use of styrene may release harmful vapor and particles. Possibly harmful airborne concentrations of evaporative droplets, or particles containing volatile organic chemicals (VOCs), occur in the reinforced plastics industry and in paint spraying, especially automobile paint spray booths. Other examples include indoor sprays such as household chemicals (air fresheners, cleaning solvents, insecticides) and products used in beauty salons (hairspray, nail dryers). Organic pesticides, such as Aldrin (TM), Lindane (TM), etc., may be sprayed on fields or used in greenhouses and may be inhaled by farm workers. Many chemicals may be in two phases, gas and particles (microscopic sized solids or liquid droplets) which enter the workplace atmosphere and may be breathed by the workers.

Current practice establishes a single standard for the airborne concentration of each chemical. However, such a standard is over-simplified for materials that are partitioned between phases. It does not take account of the difference in the quantity of inhaled material that can deposit in the different parts of the respiratory system from the two phases of many chemicals (particle and vapor) or the interaction between those particles and vapors. The American Conference of Governmental Industrial Hygienists (ACGIH) has considered in its Chemical Substances Threshold Limit Values (TLV) Committee, that dual threshold limit values (TLVs) be established for the gas-phase and particle phase of a volatile substance. However, commercially available air samplers are not adequate for efficient separation of coexisting vapor and particles due to vapor evaporation from, and absorption by, the particles' surface in the sampling process.

Gunderson and Anderson have described, and made available, a two-stage vapor/particle sampler (denuder-filter type) for separating airborne vapor molecules and particles. See E. C. Gunderson and C. C. Anderson, "Collection Device for Separating Airborne Vapor and Particulates", Am. Ind. Hyg. Assoc. J. 48: 634–638 (1987). Their denuder filter type sampler is based on the principle of different diffusion rates of the vapor and particles and applies when separating a chemical in the vapor phase from a different chemical in the particle phase. Their system will not work for volatile droplets, or particles containing volatile organic chemicals (VOCs) where the objective is to sample the separate phases of the same chemical, because a pressure gradient is established by removal of the vapor causing further evaporation from the particles. This alters the partition that was originally present and gives an incorrect result.

The following patents relate to personal air samplers and are incorporated by reference herein. In U.S. Pat. No. 4,796,475 a solid impaction plate within a chamber is positioned beneath a nozzle. The air impacts on the plate, then flows through a filter and is drawn out of the chamber. In U.S. Pat. No. 4,569,235 a constant intake flow rate is maintained during sequential air samplings, using either AC or DC power sources. In U.S. Pat. No. 4,432,248 a filter is used to remove dirt before air enters the pump. In U.S. Pat. No. 4,375,667 an air velocity sensor is used to calculate sample air flow rates.

SUMMARY OF THE INVENTION

In accordance with the present invention there is provided a portable air sampler which can accurately monitor the vapor and particle phases of VOCS. The particle cut-off size ($D_{50}$) depends on the inlet flow rate and the nozzle size. An embodiment of the air sampler has performed with excellent accuracy, for this type of device, at a flow rate of 1.8 LPM (Liters Per Minute) and a nozzle diameter of 1 mm, the $D_{50}$ being 1 μm.

The device is a relatively simple and inexpensive field air sampling device. It will provide essential data for the assessment of worker exposure to the vapor and particle phases of VOCs and important reference data for establishing dual phase threshold limit values (TLVs).

In the air sampler the particle and vapor phases are separated into two identifiable fractions due to differential inertia. The sampler may be used with any standard personal sampling pump that can provide the required flow.

The amount of the chemical collected is measured by standard analytical procedures. The sampler may also be applied for sampling particles of organic pesticides (Aldrin, Lindane, etc.) and particles that contain volatile inorganic acids (HF, HC1, $H_3PO_4$, $HNO_3$, $H_2SO_4$, etc.) or fluorides.

The air sampler operates by separating the vapor and particle-phase by differential inertia, as the air stream turns the particles tend to move forwardly in the direction of the inlet air flow, due to their greater mass, while the gas molecules follow the airstream, part of which flows sideways and upwardly, due to their lesser mass.

In the device the atmospheric air is drawn in by a suitable pump, causing a flow of air sample (Qo). The inlet flow of air enters an elongated inlet tube having a constricted outlet nozzle. The inlet tube is centered in a larger cylindrical housing which forms an anisokinetic tube ("anisokinetic"—unequal motion produced by forces). The anisokinetic tube has two outlets (exit flow paths) with the air sample flowing out of both exit flow paths. Preferably about one-half the air flows out through each path. Each flow path includes a sorbent tube. The preferred absorbent tube for VOCs contains coconut charcoal (Lot 120 (TM), SKC Inc., Eighth Four, Pa.). However, other adsorbents are more suitable for certain compounds.

A first exit path includes a particle filter for collecting particles. The nozzle of the inlet tube is directed toward the filter. The preferred filter is a glass fiber filter (Gelman Instrument Co., Ann Arbor, Minn.). Particles will strongly tend to be moved, by their inertia, into the particle filter, but only air and vapor and particles smaller than the cut size will flow out the second exit flow path. A sorbent tube positioned after the filter will collect vapor from air passing through the filter plus vapor evaporation from the particles in the filter.

BRIEF DESCRIPTION OF THE DRAWINGS

The following detailed description should be taken in conjunction with the accompanying drawings. In the drawings:

FIG. 1 is a side cross-sectional assembled view of the preferred embodiment of the air sampler of the present invention;

FIG. 2 is an exploded side cross-sectional view of the air sampler of FIG. 1; and FIG. 3 is an exploded side cross-sectional view of a second embodiment of the air sampler of the present invention.

DETAILED DESCRIPTION OF THE INVENTION

Figure 1:
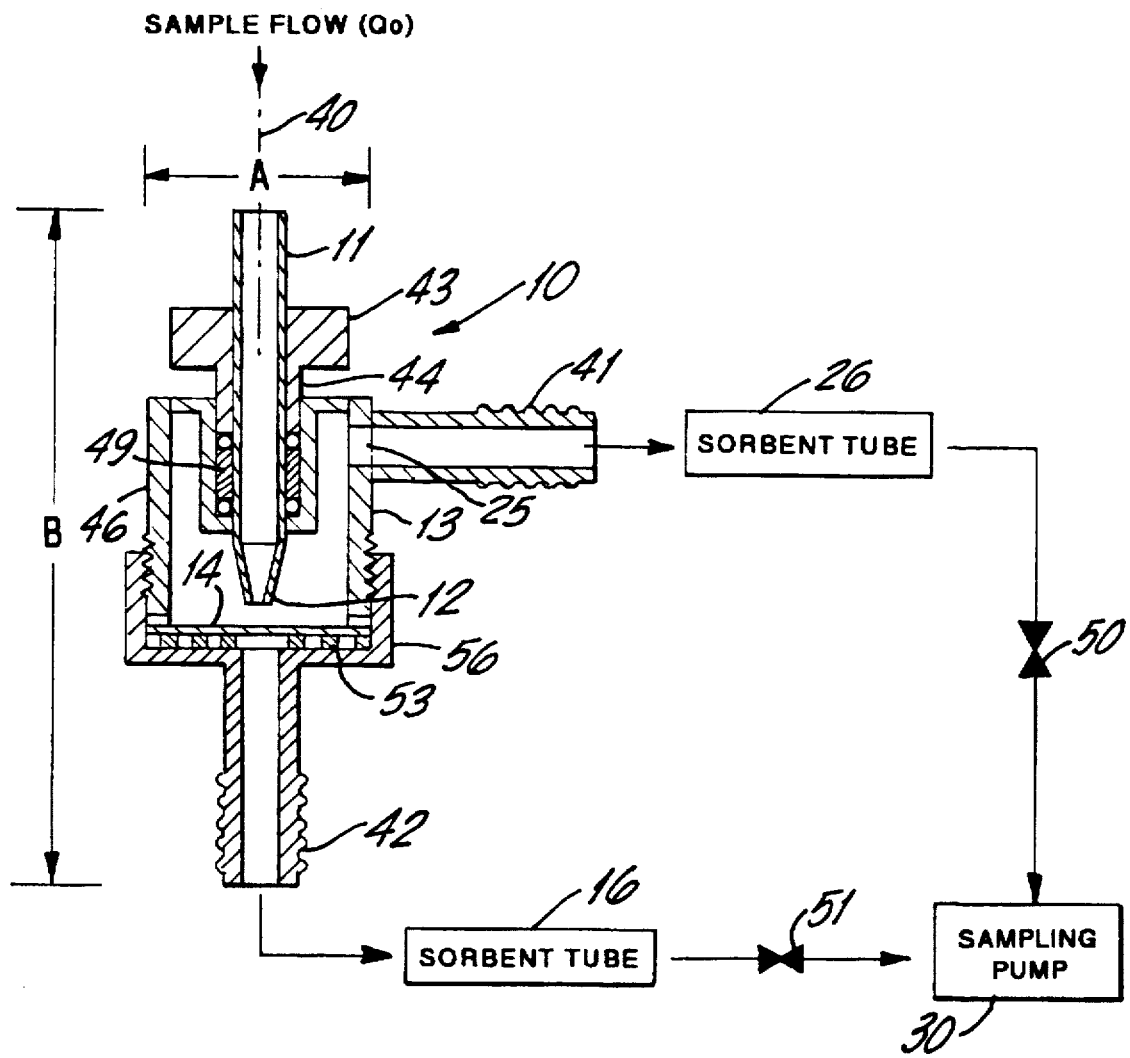
Figure 2:
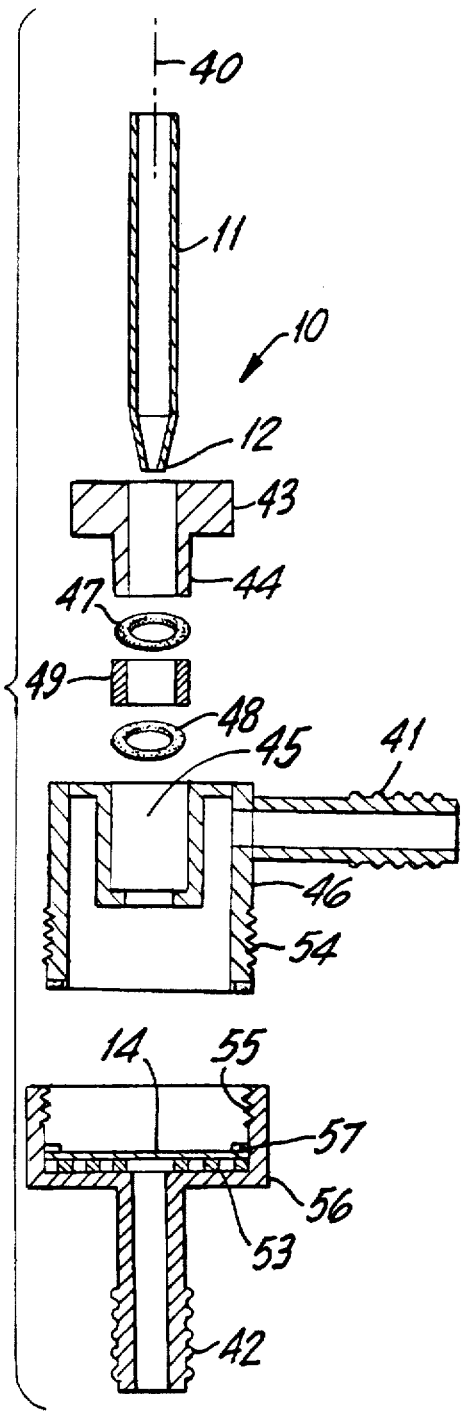
Figure 3:
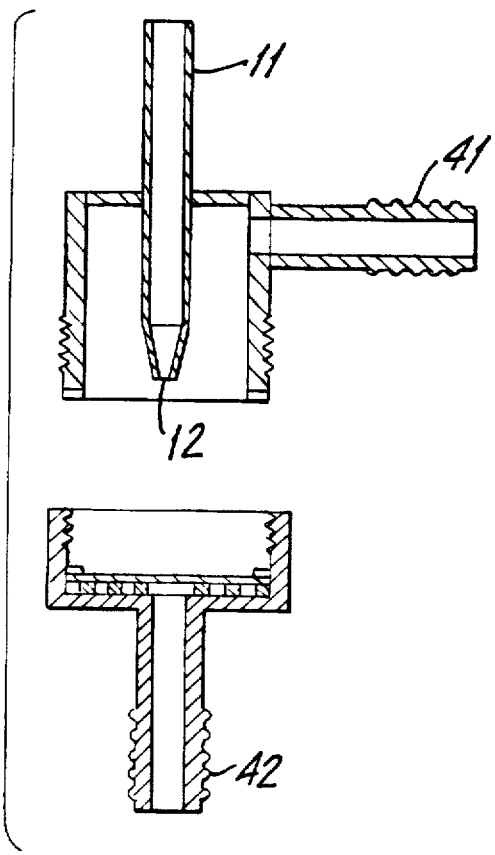

As shown in FIGS. 1 and 2 the air sampler 10 uses a conventional sampling pump 30 to apply sufficient suction, for example, 1.8 LPM (Liters Per Minute), to draw air through the sampler 10. The sample flow (Qo) of atmospheric air, for example air in a workplace, is sucked into inlet tube 11. The inlet tube 11 has a constricted outlet nozzle 12 which is within a housing 13 that acts as an anisokinetic tube. In the embodiment of FIG. 3 the inlet tube 11 is fixed with respect to the housing. The air flow depends on the nozzle size and the minimum size of the particles desired to be trapped. Generally the preferred nozzle size is 0.5 mm to 2 mm and most preferred 1.0 mm, and the preferred air flow is 0.5 to 4 LPM and most air flow preferred (for 1.0 mm nozzle) is 1.8 LPM. The housing has a larger internal diameter than the outer diameter of inlet tube 11. The nozzel 12 is directed toward a removable filter 14, to collect particles. The preferred filter is a circular glass fiber filter type 25 mm in diameter available from Gelman Instrument Co., Ann Arbor, Mich.). In the embodiment of FIGS. 1 and 2, the nozzle 12 is circular and has an internal diameter of 1.0 mm and is adjustable from 1 to 3 mm from the filter 14.

A glass tube 16 is connected to a hose connector at the bottom of housing 56 preferably using a flexible hose (not shown). The glass tube 16 is packed with a vapor absorbent material, preferably activated charcoal LOT 120 (TM) 20/40 mesh, 50/100 mg., available from SKC Inc., Eight Four, Pa., to form a first sorbent (vapor) tube (Chemical Sorbent Tube—CST). That sorbent tube 16 collects the vapor from the first flow path, which is preferably about one-half, and at least 40%, of the vapor entering the sampler 10. Sorbent tube 16 also collects vapor given off by particles that are collected by particle filter 14.

The housing 13 has a top exit orifice 25 leading to a second glass sorbent tube 26. Tube 26 is packed with a vapor absorbent material to form a second sorbent tube preferably of the same type as sorbent tube 16, i.e., a second CST (Chemical Sorbent Tube).

In operation, the user turns on the pump and air is sucked into tube 11 and exits with a predetermined velocity from nozzle 12. That velocity depends on the air flowrate (how many LPM) and the size of the exit nozzle. By the correct selection of these factors, the inertia of particles larger than a certain size (1 μm), will cause them to continue in the direction of the flow of air and be collected by filter 14. In the case of styrene, and other droplets, the particles will be caught by filter 14, then be evaporated from filter 14 and become adsorbed in sorbent tube 16. Preferably about one-half of the air and its vapor molecules will flow in a sidewise direction and out the second flow path and the vapor in that flow path is collected by CST tube 26. After the samples are collected, the glass sorbent tubes 16 and 26 are broken open and their adsorbed chemical contents, and the contents of the filter, analyzed by gas chromatography.

The preferred sampler 10 is shown in FIGS. 1 and 2. It is round in cross-sections (taken perpendicular to axis 40), has an outer diameter (O.D.) of 1⅛ inches (arrow A), a height of 2¼ inches (arrow B) and two hose connectors 41, 42 (O.D. ⁵⁄₁₆ inches). In any event, the sampler should be less than 5 inches high and 3 inches wide. A support member 43 surrounds a portion of the tube 11 and has a bushing portion 44 which fits within a cavity 45 of the upper housing member 46, using two "O" rings 47,48 and bushing 49. The upper housing member 46 has an outer diameter of 1 inch (arrow C) and exterior screw threads 54 with mate with the interior screw threads 55 of the lower housing member 56. A ring-like gasket 57 fits on top of the filter 14 which is positioned on top of filter support 53 (a series of concentric rings). Two flow controllers 50,51 (valves) are used to control the flows of air drawn by sampling pump 30. The hose connectors 41,42 are connected to hoses (not shown), the hoses and the direction of air in the hoses being indicated in FIG. 1 by lines and arrows, respectively.

Since the device operates by differential inertia (differential inertia due to difference in mass between particles and gas molecules) it may be operated in any orientation, i.e., upside down, sidewise, etc.

The air concentrations of a VOC in the two phases can be determined as:

$$C_v = (1 + \alpha)C_{CST}\#2$$
$$C_p = (C_{CST}\#1 + C_F) - \alpha C_{CST}\#2$$
$$\alpha = \frac{Q_o - Q_v}{Q_v}$$

Where, $Q_o$ is the flowrate into inlet 11 and $Q_v$ is the flowrate through the side arm sorbent tube 26; $C_v$ and $C_p$ represent the mass concentrations of VOC in the vapor phase and in the particle phase, respectively; $C_{CST}\#1$, $C_{CST}\#2$ and $C_F$ are the mass concentrations of volatile chemical collected by CST#1 (16), CST#2 (26) and the filter, respectively.

The present air sampler is a relatively simple and inexpensive personal and field sampling device. It may be used to monitor airborne VOC containing aerosols in industrial work environments, such as the reinforced plastic industry and paint spray booths and outdoors where chemicals are sprayed. It provides for the proper evaluation of worker exposure to the vapor and particle phases of a VOC and for establishing the dual TLVs of vapors and particles. This device may be applied for sampling particles that contain volatile, or semi-volatile, components, which are traditionally sampled with other sorbent collectors such as silica gel, porous polymer, etc. The duration that the sampler 10 is operated depends on the concentration of the contaminant in the ambient air and the purpose of taking the air sample. A typical use would be to clip or strap the sampler 10 to a worker during his/her eight-hour shift to determine if the air the worker breathes is within industry and/or governmental air standards for the particular chemical used in that workplace. Since phase specific standards have not yet been established for semi-volatile, or volatile, contaminants, this sampler can be used to help establish a basis for such standards.

What is claimed is:

1. An air sampler system to collect separate samples of an airborne chemical having simultaneously particles and vapor in the air, the system comprising an air sampler device comprising:

(a) a first conduit having an inlet orifice adapted to receive air drawn into the first conduit and an exit nozzle from which air exits;

(b) a housing at least partly surrounding the first conduit and having a first exit orifice, and a second exit orifice separated from the first exit orifice and not directly aligned with the nozzle;

(c) a particle filter means spaced from the nozzle, aligned with the nozzle and proximate to the nozzle, the filter means being between the nozzle and the first exit orifice, to collect the particles which will enter the filter due to inertia from their mass while vapor and air molecules due to their lower mass, compared to the mass of the particles, will flow along both conduits;

the air sampler system further comprising:

(d) a pair of vapor sorbent tubes; and (e) an air sampling pump; wherein one end of each sorbent tube is connected for air flow to the sampling pump and the opposite end of the sorbent tubes are connected, for air flow, to respective exit orifices.

2. An air sampler as in claim 1 wherein the filter is a glass fiber filter.

3. An air sampler system as in claim 1 wherein the sorbent tubes are glass tubes filled with charcoal.

* * * * *